United States Patent [19]

Maeda et al.

[11] Patent Number: 5,369,112
[45] Date of Patent: Nov. 29, 1994

[54] METHOD OF TREATING CATARACTS CAUSED BY ACTIVE OXYGEN

[75] Inventors: Hiroshi Maeda; Takaaki Akaike, both of Kumamoto; Hideo Nishigoori; Teizi Urakami, both of Tokyo; Chieko Yoshida, Niigata, all of Japan

[73] Assignee: Mitsubishi Gas Chemical Company Inc., Tokyo, Japan

[21] Appl. No.: 841,563

[22] Filed: Feb. 26, 1992

[30] Foreign Application Priority Data

Mar. 4, 1991 [JP] Japan ................................. 3-062592
Mar. 4, 1991 [JP] Japan ................................. 3-062593

[51] Int. Cl.$^5$ .............................................. A61K 31/44
[52] U.S. Cl. ...................................... 514/287; 514/912
[58] Field of Search ............................ 514/287, 912

[56] References Cited

U.S. PATENT DOCUMENTS 4,898,870 2/1990 Narutomi ............................ 514/292

FOREIGN PATENT DOCUMENTS 0262345 4/1988 European Pat. Off. .
0423012 4/1991 European Pat. Off. .
0429333 5/1991 European Pat. Off. .

OTHER PUBLICATIONS

"Collection of Summaries of Lectures (5) at 109th Meeting of Japan Pharmacological Society", p. 42, 1989.
"Current Therapeutic Research", 44:891–901 1988.
"PQQ and Quinoprotein", Jongejan, Duine, ed. pp. 162–164 (1989), Kluwer Academic Publishers.
"Life Science" 45: 593–398 (1989).
"Hiroshima J. Med. Sci" 38(1): 49–51 (1987).
Chem Abst. vol. 110, No. 4, Jan. 23, 1989 Abst. #29104N.
Chem Abst vol. 110, No. 10, Mar. 6, 1989, Abst #82492P.
Hamagishi et al, The Journal of Pharmacology and Experimental Therapeutics 255(3): 980–985, 1990.

*Primary Examiner*—Marianne M. Cintins
*Assistant Examiner*—William R. A. Jarvis
*Attorney, Agent, or Firm*—Henry T. Burke

[57] ABSTRACT

Pyrrolo quinoline esters, oxazopyrrolo quinolines and esters of oxazopyrrolo quinolines are effective at treating cataracts through their active oxygen scavenging activity.

2 Claims, No Drawings

METHOD OF TREATING CATARACTS CAUSED BY ACTIVE OXYGEN

The present invention relates to active oxygen scavengers containing pyrrolo quinoline quinone esters, oxazopyrrolo quinolines and/or oxazopyrrolo quinoline esters as active ingredients.

Human beings and other aerobic organisms inhale oxygen and utilize it for oxidation of biomaterials and synthesis of ATP, in the course of which a part of oxygen is activated to produce so-called "active oxygen".

Active oxygens include $O_2^-$ (superoxide), $H_2O_2$ (hydrogen peroxide), $\cdot OH$ (hydroxy radical), $^1O_2$ (singlet oxygen), lipoperoxy radicals (RCOOH, derivatives of $H_2O_2$), and lipoalkoxy radicals (RO·, derivatives of ·OH). It has been clear that these active oxygens peroxidize lipid in living bodies and the peroxide lipid adversely affect living bodies. Examples of the problems include senescences, geriatric diseases and metabolic diseases such as carcinogenesis, arteriosclerosis, diabetes mellitus, ischemic reperfusion, Parkinson's disease, shock, disseminated intravascular coagulation syndrome, oral diseases, lung diseases, digestive diseases, kidney diseases, cataract, and medicinal poisoning caused by bipyridyl herbicides, halogenated hydrocarbons, benzene, chloroform and the like. Furthermore, it has been known that alloxan, streptozotocin, adriamycin and daunomycin which are anticancer agents, methyldopa and hydralazine which are hypotensive agents, primaquine and pamaquine which are antimalarial agents, paracetamol and phenacetin which are analgesics, and hydrocortisone which is both anti-inflammatory and antiallergic agent cause diabetes mellitus, liver metabolic diseases, hemolysis, kidney diseases and cataract as adverse side effects. These are considered to be troubles caused by radical or active oxygen due to administered medicines.

It is known that living bodies have defensive mechanisms against harmful active oxygen and there are antioxidation enzymes such as glutathione peroxidase, catalase and superoxide dismutase and antioxidation substances for non-enzyme micromolecules such as vitamin E, ascorbic acid and glutathione and it is assumed that they substances interact with one another to perform the desired functions.

Recently, it has been discovered that pyrrolo quinoline quinone (PQQ) found as a novel coenzyme for oxidoreductases has a strong active oxygen scavenging action ("Collection of Summaries of Lectures (5) at the 109th meeting of Japan Pharmacological Society", page 42 (1989)). Furthermore, it has been reported that PQQ inhibits liver diseases caused by carbon tetrachloride, endotoxin shock and cataracts caused by hydrocortisone. [Watanabe et al, "Current Therapeutic Research", Vol.44, pp 896–901, 1988; Matsumoto et al, "PQQ and Quinoprotein" edited by Jongejan, Duine, pp 162–164, 1989 (Kluwer Academic Publishers); Nishigoori et al, "Life Science", Vol.45, pp 593–598, 1989]. Besides, recently, elucidation of physiological activity of PQQ in living bodies has been intensively studied.

This PQQ exhibits a strong active oxygen scavenging action and is useful for treatment of various diseases mentioned-above which are understood to be caused by active oxygen. However, it has been found that PQQ has kidney toxicity (Watanabe et al, "Hiroshima J. Med. Sci.", Vol.38, No.1, pp 49–51 (1987)).

Thus, therapeutic agents low in toxicity, especially kidney toxicity and having active oxygen scavenging action are found, would be useful to treat senescences, geriatric diseases and other metabolic diseases caused by active oxygen.

It has now been found that pyrrolo quinoline quinone esters, oxazopyrrolo quinolines and/or oxazopyrrolo quinoline esters are low in toxicity, have strong active oxygen scavenging effect and have inhibitory and curing effects against various diseases caused by active oxygen.

Accordingly, the present invention relates to active oxygen scavengers containing pyrrolo quinoline esters, oxazopyrrolo quinolines and/or oxazopyrrolo quinoline esters as an active ingredient.

Pyrrolo quinoline quinone esters (hereinafter referred to as "PQQ esters") are esters of PQQ and have the following formulas.

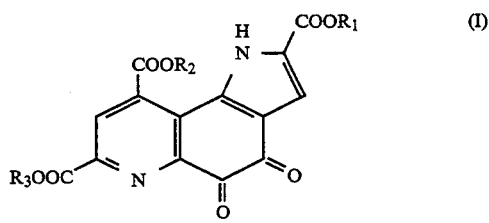

(I)

[wherein $R_1$, $R_2$ and $R_3$ represent hydrogen, alkyl, alkenyl or benzyl group and may be identical or different].

Oxazopyrrolo quinolines (hereinafter referred to as "OPQ") are 2,8,10-tricarboxy-1-H-oxazo[5,4-h]-pyrrolo[2,3-f]quinoline and its 5-substitution products and these have the following formula.

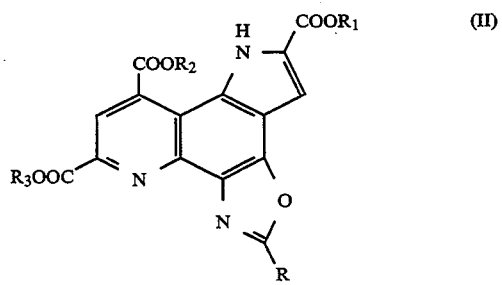

(II)

[wherein R represents hydrogen or a lower alkyl group having 1 to 4 carbon atoms which may be substituted by substituent(s), said substituent(s) being selected from the class consisting of hydroxyl, carboxyl, mercapto, amino, carbamyl, phenyl, hydroxyphenyl, guanidino, imidazolyl and methylmercapto groups, and $R_1$, $R_2$ and $R_3$ represent hydrogen, alkyl, alkenyl or benzyl group and may be identical or different].

$R_1$, $R_2$ and $R_3$ of PQQ esters used in the present invention may be identical or different and represent hydrogen or alkyl, alkenyl or benzyl group and form monoesters, diesters or triesters.

The PQQ esters can be easily produced by allowing PQQ or PQQ salt to react with alcohols by conventional process. The alkyl group of $R_1$, $R_2$ and $R_3$ in the formula [I] includes, for example, methyl and ethyl and the alkenyl group includes, for example, allyl.

The PQQ triesters can be easily produced by allowing PQQ to react with alcohols or the like (Japanese Patent Kokai Nos. 3-123781 and 3-145492). The PQQ monoesters and PQQ diesters can be obtained by partial hydrolysis of PQQ triesters under basic condition. The PQQ diesters can also be obtained by allowing PQQ monoesters to react with alcohols at optionally selected reaction temperatures and for optionally selected reaction time.

The OPQ used in the present invention can be easily produced by allowing PQQ to react with various α-amino acids, methylamine and the like in the presence of oxygen.

The OPQ in the present invention includes, for example, OPQ (R=H) obtained from a PQQ and one of glycine, threonine, tryptophan, proline, tyrosine, serine and monomethylamine (Japanese Patent Application No. 1-292459), hydroxymethyl OPQ (R=CH$_2$OH) obtained from a PQQ and serine (Japanese Patent Application No. 1-258791), 1-methylethyl OPQ (R=CH(CH$_3$)$_2$) obtained from a PQQ and valine (Japanese Patent Application No. 1-309479), 1-methylpropyl OPQ (R=CH(CH$_3$)CH$_2$CH$_3$) obtained from a PQQ and isoleucine (Japanese Patent Application No. 1-309480), 2-methylpropyl OPQ (R=CH$_2$CH(CH$_3$)$_2$) obtained from a PQQ and leucine (Japanese Patent Application No. 1-309481), methyl OPQ (R=CH$_3$) obtained from a PQQ and alanine (Japanese Patent Application No. 1-327347), 2-carboxyethyl OPQ (R=CH$_2$CH$_2$CO$_2$H) obtained from a PQQ and glutamic acid (Japanese Patent Application No. 1-327351), 2-carbamoylethyl OPQ (R=CH$_2$CH$_2$CONH$_2$) obtained from a PQQ and glutamine (Japanese Patent Application No. 1-327348), 2-methylthioethyl OPQ (R=CH$_2$CH$_2$SCH$_3$) obtained from a PQQ and methionine (Japanese Patent Application No. 1-327349), benzyl OPQ obtained from a PQQ and phenylalanine (Japanese Patent Application No. 1-327350), 4-hydroxyphenylmethyl OPQ obtained from a PQQ and tyrosine (Japanese Patent Application No. 2-107357), 1-carboxymethyl OPQ (R=CH$_2$CO$_2$H) obtained from a PQQ and aspartic acid, 1-carbamoylmethyl OPQ (R=CH$_2$CONH$_2$) obtained from a PQQ and asparagine, 1-(4-imidazolyl)methyl OPQ obtained from a PQQ and histidine, 4-aminobutyl OPQ (R=(CH$_2$)$_4$NH$_2$) obtained from a PQQ and lysine, 3-guanidinopropyl OPQ obtained from a PQQ and arginine, and 1-mercaptomethyl OPQ (R=CH$_2$SH) obtained from a PQQ and cystine. Furthermore, salts of respective OPQ include, for example, alkali metal salts, alkaline earth metal salts, ammonium salts and substituted ammonium salts and these salts are also effective as active oxygen scavengers. Typical examples thereof are sodium salts, potassium salts, magnesium salts, calcium salts, ammonium salts, trimethylammonium salts, triethylammonium salts, and triethanolammonium salts.

$R_1$, $R_2$ and $R_3$ in the esters of OPQ represented by the formula [II] may be identical or different and represent hydrogen atom or alkyl, alkenyl or benzyl group and they form monoesters, diesters and triesters. These esters of OPQ can be easily produced by allowing an OPQ or salts thereof to react with alcohols by conventional processes. The alkyl group includes, for example, methyl group and ethyl group and the alkenyl group includes, for example, allyl group. It is also possible to produce the desired esters of OPQ by allowing PQQ or PQQ salts to react with alcohols by conventional processes to obtain esters of PQQ and then allowing the esters to react with various amino acids or methylamine.

The active ingredient of the present invention may be formulated using any of a variety of optionally selected surface active agents, carriers, colorants, preservatives, coating aids and the like. Moreover, it may be used in combination with other medicines. Dosage of the active ingredient may vary depending on the identity and extent of the disease under treatment, the selected active ingredient and manner of administration. Typically, the dosage will be 1–100 mg, preferably 5–50 mg/kg (body weight/day) which may be administered once or, with divided administration, twice or three times a day.

[Membrane permeability test on PQQ and PQQ esters]

Permeability of various compounds through capsule of crystal bovine lens was examined in accordance with the method mentioned in "Crystal Lens and Biochemical Mechanism thereof" (pages 436–440) edited by Shuzo Iwata (Medical Aoi Publisher). Each compound dissolved in 10 mM HEPES buffer (containing 1% DMSO in the case of PQQ triesters) was put in an apparatus for measurement of membrane permeation constant and left to stand for 16 hours at 35° C. and then amount of the compound which migrated was measured by ultraviolet absorption (243 nm for PQQ·2Na and 255 nm for PQQ esters) to obtain membrane permeation constant.

As shown in Table 1, membrane permeation constant of PQQ triallyl ester is 3–4 times that of PQQ·2Na and those of PQQ trimethyl ester and PQQ triethyl ester were about twice that of PQQ·2Na. Thus, it can be seen that membrane permeability was markedly improved.

TABLE 1

| Compound | Membrane permeation constant ($10^{-7}$ cm$^2$ · sec$^{-1}$) |
| --- | --- |
| PQQ.2Na | 0.68 ± 0.36 |
| PQQ trimethyl ester | 1.41 ± 0.48 |
| PQQ triethyl ester | 1.22 ± 0.37 |
| PQQ triallyl ester | 2.42 ± 0.60 |

[Acute toxicity test and kidney toxicity test of PQQ, PQQ esters and OPQ]

Acute toxicity test (1)

To male mice SPF-ICR five weeks old (supplied by Japan Charles River Co.) were intraperitoneally administered PQQ·2Na, PQQ trimethyl ester, PQQ triallyl ester, OPQ, 1-methylpropyl OPQ, 2-methylthioethyl OPQ and benzyl OPQ at dosages of 40, 80, 160 and 200 mg per kg of body weight of mouce, respectively and they were bred for 14 days at 25° C. One group consisted of 8 mice. For administration, PQQ·2Na and OPQ and esters thereof were dissolved in physiological saline and PQQ trimethyl ester and PQQ triallyl ester were suspended in 1% Tween 80-containing physiological saline, respectively.

No mice died with administration of 40 mg/kg-mouse of PQQ·2Na, but five mice died with administration of 80 mg and eight mice all died with administration of 160 mg and 200 mg. LD$_{50}$ of PQQ·2Na was about 70 mg/kg-mouse. On the other hand, no mice died with administration of PQQ trimethyl ester, PQQ triallyl ester and OPQ and esters thereof. Thus, it can be seen that PQQ esters and OPQ and esters thereof are conspicuously low in toxicity as compared with PQQ.

Acute Toxicity Test (2)

To male mice SPF-ICR five weeks old (supplied by Japan Charles River Co.) were intraperitoneally administered PQQ triallyl ester at dosages of 40, 80, 160, 200, 400 and 800 mg per kg of body weight of mouse, respectively and they were bred for 14 days at 25° C. One group consisted of 8 mice. For administration, PQQ triallyl ester was suspended in 1% Tween 80-containing physiological saline.

No mice died with administration of 200 mg or less of PQQ triallyl ester, but three mice died with administration of 400 mg and eight mice all died with administration of 800 mg. $LD_{50}$ was 10 about 500 mg/kg-mouse.

Acute Toxicity Test (3)

To male mice SPF-ICR five weeks old (supplied by Japan Charles River Co.) was intraperitoneally administered OPQ at dosages of 0.1, 0.2, 0.4, 0.8, and 1.2 g per kg of body weight of mouse, respectively and they were bred for 14 days at 25° C. One group consisted of 8 mice. No mice died with administration of 0.1–0.4 g and two mice died with administration of 0.8 g, three mice died with administration of 1.0 g and six mice died with administration of 1.2 g. $LD_{50}$ was about 1.0 g/kg-mouse.

Acute Toxicity Test (4)

To male mice SPF-ICR five weeks old (supplied by Japan Charles River Co.) was orally administered OPQ at dosages of 1.0, 1.5 and 2.0 g per kg of body weight of mouse, respectively and they were bred for 14 days at 25° C. One group consisted of 8 mice. No mice died.

Kidney Toxicity Determined by Urine Test

PQQ·2Na, PQQ trimethyl ester, PQQ triallyl ester and OPQ and esters thereof were intraperitoneally administered to mice and they were bred in the same manner as in the above acute toxicity test. Urine of the mice was taken every day and glucose concentration was measured using clinical examination reagent (trademark: URISTICKS 2 manufactured by Miles.Sankyo Co.). As shown in Table 2, glucose was detected in urine of mice to which PQQ·2Na was administered while no glucose was detected in urine of all mice to which PQQ trimethyl ester or OPQ or esters thereof were administered. That is, PQQ showed kidney toxicity, but PQQ esters and OPQ and esters thereof did not show kidney toxicity.

TABLE 2

| Administration | Elapsed days (day) | | | | | | | | |
|---|---|---|---|---|---|---|---|---|---|
| of compound | 1 | 2 | 3 | 6 | 7 | 8 | 10 | 13 | 14 |
| No administration | – | – | – | – | – | – | – | – | – |
| PQQ·2Na | | | | | | | | | |
| 20 mg/kg | – | – | – | – | – | – | – | – | – |
| 40 mg/kg | 3+ | 4+ | 4+ | 3+ | ± | ± | ± | ± | – |
| 80 mg/kg | 4+ | 4+ | 4+ | 3+ | + | ± | – | – | – |
| PQQ trimethyl esters | | | | | | | | | |
| 20 mg/kg | – | – | – | – | – | – | – | – | – |
| 40 mg/kg | – | – | – | – | – | – | – | – | – |
| 80 mg/kg | – | – | – | – | – | – | – | – | – |
| 160 mg/kg | – | – | – | – | – | – | – | – | – |
| 200 mg/kg | – | – | – | – | – | – | – | – | – |
| 400 mg/kg | – | – | – | – | – | – | – | – | – |
| 1000 mg/kg | – | – | – | – | – | – | – | – | – |
| PQQ triallyl ester | | | | | | | | | |
| 20 mg/kg | – | – | – | – | – | – | – | – | – |
| 40 mg/kg | – | – | – | – | – | – | – | – | – |
| 80 mg/kg | – | – | – | – | – | – | – | – | – |
| 160 mg/kg | – | – | – | – | – | – | – | – | – |
| 200 mg/kg | – | – | – | – | – | – | – | – | – |
| 400 mg/kg | – | – | – | – | – | – | – | – | – |
| 1000 mg/kg | – | – | – | – | – | – | – | – | – |
| OPQ | | | | | | | | | |
| 20 mg/kg | – | – | – | – | – | – | – | – | – |
| 40 mg/kg | – | – | – | – | – | – | – | – | – |
| 80 mg/kg | – | – | – | – | – | – | – | – | – |
| 160 mg/kg | – | – | – | – | – | – | – | – | – |
| 200 mg/kg | – | – | – | – | – | – | – | – | – |
| 400 mg/kg | – | – | – | – | – | – | – | – | – |
| 800 mg/kg | – | – | – | – | – | – | – | – | – |
| 1000 mg/kg | – | – | – | – | – | – | – | – | – |
| 1200 mg/kg | – | – | – | – | – | – | – | – | – |
| 1-methylpropyl OPQ | | | | | | | | | |
| 20 mg/kg | – | – | – | – | – | – | – | – | – |
| 40 mg/kg | – | – | – | – | – | – | – | – | – |
| 80 mg/kg | – | – | – | – | – | – | – | – | – |
| 160 mg/kg | – | – | – | – | – | – | – | – | – |
| 200 mg/kg | – | – | – | – | – | – | – | – | – |
| 2-methylethyl OPQ | | | | | | | | | |
| 20 mg/kg | – | – | – | – | – | – | – | – | – |
| 40 mg/kg | – | – | – | – | – | – | – | – | – |
| 80 mg/kg | – | – | – | – | – | – | – | – | – |
| 160 mg/kg | – | – | – | – | – | – | – | – | – |
| 200 mg/kg | – | – | – | – | – | – | – | – | – |
| Benzyl OPQ | | | | | | | | | |
| 20 mg/kg | – | – | – | – | – | – | – | – | – |
| 40 mg/kg | – | – | – | – | – | – | – | – | – |
| 80 mg/kg | – | – | – | – | – | – | – | – | – |
| 160 mg/kg | – | – | – | – | – | – | – | – | – |
| 200 mg/kg | – | – | – | – | – | – | – | – | – |

– No glucose was detected.
± 0.10 g/dl
+ 0.25 g/dl
2+ 0.50 g/dl
3+ 1.00 g/dl
4+ 2.00 g/dl Kidney Toxicity Determined by Blood Examination (1)

PQQ·2Na, PQQ triallyl ester and OPQ and esters thereof were administered to mice and they were bred in the same manner as in the acute toxicity test.

After lapse of one day from the administration, the mice were fasted (with feeding only water) and then after 18 hours, blood was collected and serum was obtained therefrom. Glucose, urea nitrogen and creatinine in the serum were examined by clinical examination reagent (trademark: FUJI DRYCHEMSLIDE manufactured by Fuji Photo Film Co., Ltd.). The results in average value of eight mice are shown in Table 3.

TABLE 3

| Administration of compound (mg/kg) | Glucose (mg/dl) | Urea nitrogen (mg/dl) | Creatinine (mg/dl) |
|---|---|---|---|
| No administration | 79 ± 10 | 23 ± 3 | 0.82 ± 0.08 |
| PQQ·2Na | | | |
| 20 | 70 ± 13 | 25 ± 3 | 0.8 ± 0.1 |
| 40 | 60 ± 12 | 110 ± 38 | 2.3 ± 1.0 |
| 80 | 57 ± 15 | 130 ± 18 | 3.4 ± 0.4 |
| 160 | 35 ± 7 | 139 ± 3 | 4.1 ± 0.2 |
| PQQ triallyl ester | | | |
| 40 | 42 ± 6 | 11 ± 4 | 0.3 ± 0.1 |
| 90 | 47 ± 15 | 12 ± 3 | 0.2 ± 0.1 |
| 160 | 59 ± 16 | 10 ± 1 | 0.1 ± 0.1 |
| 200 | 76 ± 6 | 9 ± 1 | 0.1 ± 0.1 |
| OPQ | | | |
| 40 | 90 ± 18 | 25 ± 3 | 0.70 ± 0.10 |
| 80 | 86 ± 10 | 23 ± 4 | 0.80 ± 0.10 |
| 160 | 90 ± 23 | 27 ± 6 | 0.73 ± 0.09 |
| 200 | 85 ± 24 | 28 ± 4 | 0.81 ± 0.08 |
| 1-methylpropyl OPQ | | | |
| 40 | 87 ± 20 | 26 ± 1 | 0.80 ± 0.08 |
| 80 | 104 ± 19 | 22 ± 3 | 0.78 ± 0.04 |
| 160 | 87 ± 22 | 27 ± 4 | 0.78 ± 0.04 |

TABLE 3-continued

| Administration of compound (mg/kg) | Glucose (mg/dl) | Urea nitrogen (mg/dl) | Creatinine (mg/dl) |
|---|---|---|---|
| 200 | 66 ± 11 | 27 ± 6 | 0.83 ± 0.17 |
| 2-methylthioethyl OPQ | | | |
| 40 | 96 ± 26 | 26 ± 4 | 0.76 ± 0.05 |
| 80 | 88 ± 29 | 26 ± 5 | 0.68 ± 0.08 |
| 160 | 97 ± 22 | 26 ± 3 | 0.64 ± 0.05 |
| 200 | 72 ± 16 | 26 ± 2 | 0.73 ± 0.06 |
| Benzyl OPQ | | | |
| 40 | 90 ± 24 | 23 ± 3 | 0.68 ± 0.05 |
| 80 | 87 ± 17 | 23 ± 2 | 0.68 ± 0.04 |
| 160 | 87 ± 21 | 26 ± 3 | 0.68 ± 0.08 |
| 200 | 84 ± 18 | 25 ± 3 | 0.73 ± 0.05 |

Sharp reduction of glucose and much increase of urea nitrogen and creatinine were seen and kidney toxicity was recognized when PQQ·2Na was administered. On the other hand, when PQQ triallyl ester and OPQ and esters thereof were administered, contents of glucose, urea nitrogen and creatinine were nearly the same as those in the case of administration of no compounds and kidney toxicity was not seen.

Kidney Toxicity Determined by Blood Examination (2)

PQQ trimethyl ester was administered to mice and they were bred in the same manner as in the acute toxicity test. Dosages were 150, 400 and 1000 mg per kg of body weight of mouse.

After lapse of one day from the administration, the mice were fasted (with feeding only water) and then after 15 hours, blood was collected and serum was obtained therefrom. Glucose, urea nitrogen and creatinine in the serum were examined by clinical examination reagent (trademark: FUJI DRYCHEMSLIDE manufactured by Fuji Photo Film Co., Ltd.). The results in average value of eight mice are shown in Table 4.

TABLE 4

| Administration of compound (mg/kg) | Glucose (mg/dl) | Urea nitrogen (mg/dl) | Creatinine (mg/dl) |
|---|---|---|---|
| No administration | 149 ± 57 | 22 ± 1 | 0.08 ± 0.06 |
| PQQ trimethyl ester | | | |
| 150 | 154 ± 23 | 23 ± 2 | 0.85 ± 0.08 |
| 400 | 117 ± 21 | 20 ± 2 | 0.73 ± 0.05 |
| 1000 | 125 ± 17 | 17 ± 4 | 0.73 ± 0.05 |

No kidney toxicity was recognized even when PQQ trimethyl ester was administered at a dose of 1000 mg/kg-mouse.

Kidney Toxicity Determined by Blood Examination (3)

OPQ was intraperitoneally administered to mice at dosages of 150, 300, 400 and 600 mg/kg-mouse and they were bred for one day in the same manner as in the acute toxicity test.

Thereafter, the mice were fasted (with feeding only water) and then after 18 hours, blood was collected and serum was obtained therefrom. Glucose, urea nitrogen and creatinine in the serum were examined by clinical examination reagent (trademark: FUJI DRYCHEMSLIDE manufactured by Fuji Photo Film Co., Ltd.). The results in average value of eight mice are shown in Table 5.

TABLE 5

| Administration of compound (mg/kg · mouse) | Glucose (mg/dl) | Urea nitrogen (mg/dl) | Creatinine (mg/dl) |
|---|---|---|---|
| No administration | 105 ± 29 | 28 ± 4 | 0.78 ± 0.04 |
| OPQ | | | |
| 150 | 106 ± 21 | 32 ± 3 | 0.75 ± 0.05 |
| 300 | 80 ± 15 | 29 ± 2 | 0.78 ± 0.04 |
| 400 | 104 ± 18 | 29 ± 3 | 0.78 ± 0.04 |
| 600 | 74 ± 11 | 32 ± 5 | 0.78 ± 0.11 |

For any dosages, contents of glucose, urea nitrogen and creatinine were nearly the same as those when no compounds were administered.

From the results of the urea and blood examinations, PQQ showed kidney toxicity, but PQQ esters and OPQ and esters thereof showed no kidney toxicity.

The following nonlimiting examples show active oxygen scavenging action and inhibitory and curing activities of the PQQ esters and OPQ and esters thereof of the present invention against various diseases caused by active oxygen.

EXAMPLE 1

Superoxide Scavenging Activity of PQQ Esters

Activity of PQQ esters to scavenge superoxide ($O_2^-$) produced in the system of hypoxanthinexanthine oxidase was examined by spin trapping method [using 5,5-dimethyl-1-pyrroline-N-oxide (hereinafter referred to as "DMPO") as a spin trapping agent] where electron spin resonance (hereinafter referred to as "ESR") was used.

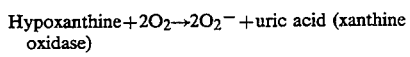

Hypoxanthine + 2O$_2$ → 2O$_2^-$ + uric acid (xanthine oxidase)

The following reagents were successively put in a test tube and stirred after addition of the hypoxanthine ⑦ to initiate the reaction and the reaction mixture was transferred to a quartz cell used for measurement of ESR. After 1 minute from initiation of the reaction, ESR was measured and comparison was made on concentration of the test compound required to reduce the produced superoxide to ½ (IC50 value).

As test compounds, PQQ esters and ascorbic acid (control) were used and scavenging activity thereof for superoxide was determined at five kinds of concentrations and IC50 was calculated.

| Reaction liquid | |
|---|---|
| ① 50 mM sodium phosphate buffer solution (pH 7.3) | 50 μl |
| ② 10 mM diethylenetriaminepentaacetic acid (hereinafter referred to as "DTPA") | 10 μl |
| ③ Xanthine oxidase (2 U/ml) | 20 μl |
| ④ Distilled water | 50 μl |
| ⑤ Test compound (2% DMSO solution) | 50 μl |
| ⑥ 900 mM DMPO | 10 μl |
| ⑦ 7.3 mM hypoxanthine | 10 μl |
| Conditions for measurement of ESR | |
| Magnetic field | 236.1 ± 5 mM |
| Output | 10 mW |
| Modulation | 100 kHz, 0.079 mT |
| Response time | 0.3 second |
| Sweeping time | 2 minutes (interval of 10 mT) |
| Amplification ratio | 500 |

The results are shown in Table 6.

TABLE 6

| Compound | $O_2^-$ scavenging activity $IC_{50}$ (× $10^{-7}$M) |
|---|---|
| Ascorbic acid | 245 |
| PQQ.2Na | 0.383 |
| PQQ monomethyl ester | 0.609 |
| PQQ dimethyl ester | 0.106 |
| PQQ trimethyl ester | 0.185 |
| PQQ triallyl ester | 0.124 |
| PQQ tribenzyl ester | 0.769 |

$IC_{50}$ of PQQ esters was 1/300–1/2000 of $IC_{50}$ of ascorbic acid. PQQ esters had strong superoxide scavenging activity of as high as 300–2000 times that of ascorbic acid.

EXAMPLE 2

Superoxide Scavenging Activity of OPQ and Esters Thereof

Superoxide scavenging activity of OPQ and esters thereof was examined in the same manner as in Example 1. The results are shown in Table 7.

$IC_{50}$ of OPQ and esters thereof was 1/5–1/20 of $IC_{50}$ of ascorbic acid. OPQ and esters thereof had strong superoxide scavenging activity of 5–20 times that of ascorbic acid.

TABLE 7

| Compound | $O_2^-$ scavenging activity $IC_{50}$ (× $10^{-6}$M) |
|---|---|
| Ascorbic acid | 24.5 |
| OPQ | 1.22 |
| Methyl OPQ | 1.64 |
| 2-Carboxyethyl OPQ | 2.96 |
| Benzyl OPQ | 3.01 |
| 1-Methylethyl OPQ | 3.14 |
| 2-Carbamoylethyl OPQ | 3.20 |
| Hydroxymethyl OPQ | 3.52 |
| 1-Methylpropyl OPQ | 3.53 |
| 2-Methylthioethyl OPQ | 3.94 |
| 4-Hydroxyphenylmethyl OPQ | 4.12 |
| 2-Methylpropyl OPQ | 4.88 |
| OPQ triallyl ester | 2.39 |

EXAMPLE 3

Hydroxy Radical Scavenging Activity of PQQ Esters

Activity of PQQ esters to scavenge hydroxy radical (·OH) produced in the system of $H_2O_2$—($Fe^{2+}$-DTPA) was examined by spin trapping method [using 5,5-dimethyl-1-pyrroline-N-oxide (hereinafter referred to as "DMPO") as a spin trapping agent] where electron spin resonance (hereinafter referred to as "ESR") was used. DTPA means diethylenetriamine-pentaacetic acid.

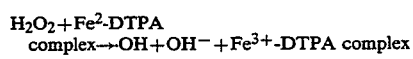

The following reagents were successively put in a test tube and stirred after addition of $H_2O_2$ ⑥ to initiate the reaction and the reaction mixture was transferred to a quartz cell used for measurement of ESR. After 1 minute from initiation of the reaction, ESR was measured and comparison was made on concentration of the test compound required to reduce the concentration of the produced hydroxy radical to ½ ($IC_{50}$ value).

As test compounds, PQQ esters and ascorbic acid (control) were used and scavenging activity thereof for hydroxy radical was determined at five kinds of concentrations and $IC_{50}$ was calculated.

| Reaction liquid | | |
|---|---|---|
| ① 50 mM sodium phosphate buffer solution (pH 7.3) | | 50 μl |
| ② 1 mM $Fe^{2+}$-DTPA complex | | 10 μl |
| ③ Distilled water | | 70 μl |
| ④ Test compound (2% DMSO solution) | | 50 μl |
| ⑤ 900 mM DMPO | | 10 μl |
| ⑥ 10 mM $H_2O_2$ | | 10 μl |
| Conditions for measurement of ESR | | |
| Magnetic field | 336 ± 5 mT | |
| Output | 10 mW | |
| Modulation | 100 kHz, 0.1 mT | |
| Response time | 0.1 second | |
| Sweeping time | 1 minute (interval of 10 mT) | |
| Amplification ratio | 125 | |

The results are shown in Table 8.

TABLE 8

| Compound | ·OH scavenging activity $IC_{50}$ (× $10^{-4}$M) |
|---|---|
| Ascorbic acid | 1.1 |
| DMSO | 150 |
| PQQ.2Na | 0.64 |
| PQQ triallyl ester | 0.42 |
| PQQ tribenzyl ester | 0.31 |

$IC_{50}$ of PQQ esters was nearly the same as that of ascorbic acid and PQQ·2Na. PQQ esters had strong hydroxy radical scavenging activity like ascorbic acid.

EXAMPLE 4

Hydroxy Radical Scavenging Activity of OPQ and Esters Thereof

Hydroxy radical scavenging activity of OPQ and esters thereof was examined in the same manner as in Example 3. The results are shown in Table 9.

TABLE 9

| Compound | ·OH scavenging activity $IC_{50}$ (× $10^{-4}$M) |
|---|---|
| Ascorbic acid | 1.0 |
| 2-Carboxyethyl OPQ | 1.10 |
| Methyl OPQ | 1.53 |
| 2-Carbamoylethyl OPQ | 1.94 |
| OPQ | 1.98 |
| 1-Methylethyl OPQ | 2.00 |
| 2-Methylthioethyl OPQ | 2.00 |
| Benzyl OPQ | 2.11 |
| 1-Methylpropyl OPQ | 2.52 |
| Hydroxymethyl OPQ | 3.05 |
| 4-Hydroxyphenylmethyl OPQ | 3.14 |
| 2-Methylpropyl OPQ | 4.21 |

$IC_{50}$ of OPQ and esters thereof was nearly the same as that of ascorbic acid. OPQ and esters thereof had strong hydroxy radical scavenging activity like ascorbic acid.

EXAMPLE 5

Pharmacological Effect of PQQ Esters and OPQ and Esters Thereof on Hydrocortisone-Induced Cataract of Hen's Eggs Fertilized eggs of white leghorn were incubated in an incubator at a temperature of 37° C. and 70% in humidity. The day on which the incubation was started was taken to be one day old. Twenty-five eggs of 15 day old were prepared and divided into 7 groups, each of which included 5 eggs (A–G). A small hole was bored through the eggshell above air chamber of the eggs of groups B–G and 0.25 μmole (as 0.2 ml solution) of hydrocortisone sodium succinate was administered into the air chamber through the hole and then, the hole was sealed with a cellophane tape. To The eggs of groups C-G was administered 1 μmole of following compounds after 3, 10 and 20 hours from administration of hydrocortisone sodium succinate. That is, 0.2 ml of a solution of PQQ·2Na in distilled water was administered to the eggs of group C, 0.2 ml of a suspension of PQQ trimethyl ester in 1% Tween 80 solution was administered to the eggs of group D, 0.2 ml of a suspension of triallyl ester in 1% Tween 80 solution was administered to the eggs of group E, 0.2 ml of a solution of OPQ in 10 mM NaCO₃ solution was administered to the eggs of group F, and 0.2 ml of a solution of methyl OPQ in 10 mM NaCO₃ solution was administered to the eggs of group G.

Crystal lens was taken out after 48 hours from administration of hydrocortisone sodium succinate and degree of cataract was judged by the criteria according to the Nishigori et al method (Nishigori et al, "Investigative Ophthalmology & Visual Science", Vol. 25, page 1051, 1984).

Criteria for Judgement

① No haze was seen in crystal lens.
② Slight opaque ring was seen in crystal lens.
③ Clear ring of white haze was seen in crystal lens.
④ White haze of pinhole size was seen in nucleus.
⑤ The whole nucleus was hazed in white.

The results are shown in Table 10.

TABLE 10

| Group | ① | ② | ③ | ④ ~ ⑤ |
|---|---|---|---|---|
| A (Blank) | 5/5 | | | |
| B (Control) | | | | 5/5 |
| C (PQQ·2Na was administered) | 1/5 | 2/5 | | 2/5 |
| D (PQQ trimethyl ester was administered) | 1/5 | | 1/5 | 3/5 |
| E (PPQ triallyl ester was administered) | 2/5 | 1/5 | 1/5 | 1/5 |
| F (OPQ was administered) | | 1/5 | 1/5 | 3/5 |
| G Methyl OPQ was administered) | 1/5 | | 2/5 | 2/5 |

TABLE 10-continued

| Group | ① | ② | ③ | ④ ~ ⑤ |
|---|---|---|---|---|

PQQ esters and OPQ and esters thereof showed clear control action on cataract like PQQ. It is considered that PQQ esters and OPQ and esters thereof scavenged active oxygen caused by hydrocortisone.

What is claimed is:

1. A method of treating cataracts caused by active oxygen in a patient in need of such treatment comprising administering to said patient a therapeutically effective amount of at least one compound selected from the group consisting of compounds represented by the formula:

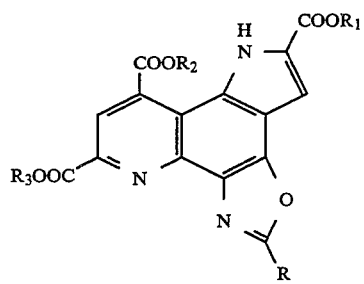

wherein R represents hydrogen or a substituted or unsubstituted lower alkyl group having 1 to 4 carbon atoms, said substituent being selected from the group consisting of hydroxyl, carboxyl, mercapto, amino, carbamyl, phenyl, hydroxyphenyl, guanidino, imidazolyl and methylmercapto groups; and $R_1$, $R_2$ and $R_3$ which may be the same or different, represent hydrogen, lower alkyl, allyl or benzyl.

2. The method according to claim 1 wherein the compound is represented by the formula:

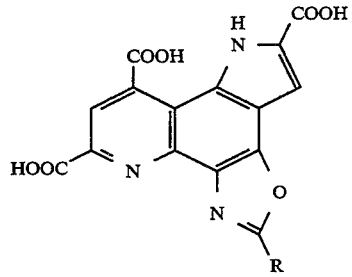

wherein R is hydrogen or methyl.

* * * * *